US006627660B1

(12) United States Patent
Piccariello et al.

(10) Patent No.: US 6,627,660 B1
(45) Date of Patent: Sep. 30, 2003

(54) STABILIZED THYROXINE COMPOUNDS

(75) Inventors: Thomas Piccariello, Blacksburg, VA (US); Anne F. LeClercq, Blacksburg, VA (US)

(73) Assignee: New River Pharmaceuticals Inc., Radford, VA (US)

( * ) Notice: Subject to any disclaimer, the term of this patent is extended or adjusted under 35 U.S.C. 154(b) by 0 days.

(21) Appl. No.: 09/440,635

(22) Filed: Nov. 16, 1999

(51) Int. Cl.[7] .................. A61K 9/20; A61K 9/14; A61K 31/195
(52) U.S. Cl. ............. 514/567; 514/109; 514/103; 514/104; 514/114; 514/140; 514/141; 514/2; 424/464; 424/465; 424/479; 424/451
(58) Field of Search ............... 514/109, 103, 514/114, 104, 140, 141, 567, 2; 530/324, 326, 327; 424/464, 465, 479, 451

(56) References Cited

U.S. PATENT DOCUMENTS

| 4,358,604 A | 11/1982 | Albarella et al. |
| 4,399,121 A | 8/1983 | Albarella et al. |
| 4,426,453 A | 1/1984 | Cree et al. |
| 4,490,221 A | 12/1984 | Collange et al. |
| 4,766,121 A | 8/1988 | Ellis et al. |
| 5,225,204 A | 7/1993 | Chen et al. |
| 5,707,979 A | * 1/1998 | Peyman et al. ............ 514/110 |
| 5,910,569 A | 6/1999 | Latham et al. |
| 5,955,105 A | 9/1999 | Mitra et al. |

FOREIGN PATENT DOCUMENTS

WO  97/21993  * 6/1997

OTHER PUBLICATIONS

Hoffenberg et al, Mass Spectrom. Biochem. Med, Symp (1974), meeting 1973, 303–12.*
Hoffenberg et al (Mass Spectrom. Biochem. Med, symp (1974), meeting 1973, 303–12) 4181–4184 (abstract).*
Bennett et al (Journal of Medicinal and Pharamceutical Chemistry 1960:2(5); 493–498).*
Bennett et al, Chemical Abstracts 8303, 1960.*
Ueki et al, Tetrahedron Letters, 27(35):4181–4184 (1986).*
Greene et al, Protective Groups in Organic Synthesis, 2nd ed, ch 3, 1991 pp. 143–148, 160–162, 167–170.*
*Methylphosphinyl (Dmp): A New Protecting Group of Tyrosine Suitable for Peptide Synthesis by Use of BOC–Amino Acids*, M. Ueki et al., Tetrahedron Letters, vol. 27, No. 35, pp. 4181–4184, 1986.

* cited by examiner

*Primary Examiner*—Russell Travers
*Assistant Examiner*—Shahnam Sharareh
(74) *Attorney, Agent, or Firm*—Hunton & Williams LLP

(57) ABSTRACT

Throxinyldimethylphosphinate was invented as a prodrug to stabilize thyroxine, a drug widely used to treat hypothyroidism. The presence of the dimethylphosphinate group at the phenolic hydroxyl of thyroxine is key to preventing thyroxine from decomposing through the proposed pathway. The prodrug will be hydrolyzed in the stomach or the gut into thyroxine and the biologically inert dimethylphosphinic acid. Related products may be stabilized with the same or similar protecting groups.

108 Claims, 3 Drawing Sheets

STABILIZED THYROXINE COMPOUNDS

FIELD OF THE INVENTION

This invention relates to the use of a phosphinate protecting group to stabilize thyroxine and related compounds, thus extending the shelf life of the drugs.

BACKGROUND OF THE INVENTION

Hypothyroidism is the most common disorder of the thyroid and is manifested through the thyroid gland's inability to produce sufficient thyroid hormone, primarily 3, 3', 5-triiodothyronine (also known as T3). Symptoms associated with hypothyroidism include cold intolerance, lethargy, fatigue, chronic constipation and a variety of hair and skin changes. Although none of these conditions are life threatening, the disease, left untreated, could result in myxedema, coma, or death.

The cause of hypothyroidism in the U.S. is brought about by either autoimmune destruction of the thyroid tissue (Hashimoto's disease), $^{131}$I therapy, or ablative surgery. It is estimated that 8 to 10 million people in the United States have low thyroid gland function, but only about 4 to 5 million hypothyroid cases have been diagnosed and treated. The prevalence of hypothyroidism increases with age, particularly within the female population.

The modern history of thyroid medication starts in the 1890's when desiccated pig thyroid was used to treat hypothyroidism. Thyroxine (3,3',5,5'-tetraiodothyronine), also known as T4, was introduced over forty years ago as a means to deliver the T3 hormone slowly without subjecting the patient to a transient hyperthyroid state. A synthetic drug based on blending T3 with T4 in a biomimetic fashion was introduced as an improved version. The medical community has discouraged this regimen, however, due to its potential for life-threatening T3 spikes.

More recently, Synthroid, a synthetic T4 compound, has captured more than 70% of the hypothyroidism market. Synthroid's sales are reported to be in excess of $500 million (with additional sales in the market being taken by generic versions of thyroxine).

Although T4 is a safe and effective way to treat hypothyroidism, a potential problem exists. Sufficient data has been generated that shows that Synthroid has a relatively short shelf life. The FDA has recommended that manufacturers of thyroid drugs address this problem.

U.S. Pat. No. 5,225,204 is directed to improving the stability of levothyroxine sodium. This patent indicates that the stability of the levothyoxine is affected by the presence of some carbohydrate excipients, such as dextrose, starch, sugar, and lactose. This patent claims that stability is achieved through mixing the levothyroxine with a cellulose carrier, with or without the addition of either polyvinyl pyrrolidine (PVP) or a Poloxamer.

U.S. Pat. No. 5,955,105 is also directed to providing an improved, stable, solid dosage form of thyroid hormone pharmaceutical preparations. This patent claims pharmaceutical preparations of thyroxine drugs including a water soluble glucose polymer and a partially soluble or insoluble cellulose polymer to provide the stability. The indicated stability is determined as an absence of potency loss when the preparation is stored at 40 degrees C. and 75% relative humidity for six months. U.S. Pat. No. 5,955,105 is hereby incorporated by reference, particularly for its teachings on components of and production of pharmaceutical preparations of thyroxine drugs.

It has been reported that the major product of T4 decomposition is diiodotyrosine (DIT). Latham, et al., showed that T4 in the blood decomposes into quinone-containing molecules. Both of these reports lead to the conclusion, heretofore unreported, that the pathway for T4 decomposition goes through a hydrolysis step with the loss or cleavage of an iodide. The energy required to cleave an $sp^2$-hybridized iodide-carbon bond, as in the case of T4, is not available under ambient conditions. As shown in FIG. 1, tautomerization prior to hydrolysis is required in order for T4 to decompose into DIT and iodoquinone. In other words, the spontaneous tautomerization of T4 is the "trigger" for its decomposition.

The energy required to cleave a phosphorus-oxygen bond is greater than that for breaking a hydrogen-oxygen bond. The utility of the present invention resides in the prevention of tautomerization by replacing the hydrogen on the phenolic hydroxyl with a phosphinate group. By preventing tautomerization (as shown in FIG. 3), the hydrolysis step cannot take place, thereby, reducing the lability of T4 to hydrolysis and increasing its shelf life.

The dimethylphosphinate group has been used as a protecting group for tyrosine in peptide synthesis. Ueki et al., *Tetrahedron Letters* 27(35):4181–4184 (1986). The purpose of this group, however, was only to offer protection during peptide synthesis. It was not used to stabilize any other compounds, and was used only as part of a step during synthesis, never as a compound for use as a pharmaceutical composition. One aspect of the present invention is that it was not heretofore appreciated that stabilization was necessary in thyroid hormones. This problem is herein both recognized and solved by the use of phosphinate (and possibly other) protecting groups on the phenolic hydrogen. The resulting protected hormone is not deprotected in vitro. Rather, the hormone or hormone precursor is ingested while still protected by the phosphinate group.

The result of the present invention is a prodrug to a thyroid hormone, which will be converted to the thyroid hormone in vivo after being provided to the patient in a hypothyroidism treatment regimen. The prodrug will be hydrolyzed in the stomach or the gut into thyroxine and the biologically inert dimethylphosphinic acid. This provides a drug with all the therapeutic advantages of Synthroid with the additional advantage of increased stability, i.e., longer shelf life. Another advantage is that a thyroxine product with increased stability will be useful in producing either an injectable product or an oral suspension (suitable for children)—both of which are desirable. Yet another advantage of the present invention is a method to stabilize and increase the shelf life of thyroxine and related thyroid hormone compounds.

The compounds of the present invention may be provided in several useful forms, including pharmaceutical compositions in the form of ingestable tablets, oral suspension, or intravenous solutions.

DESCRIPTION OF THE PREFERRED EMBODIMENTS

Figure 1:
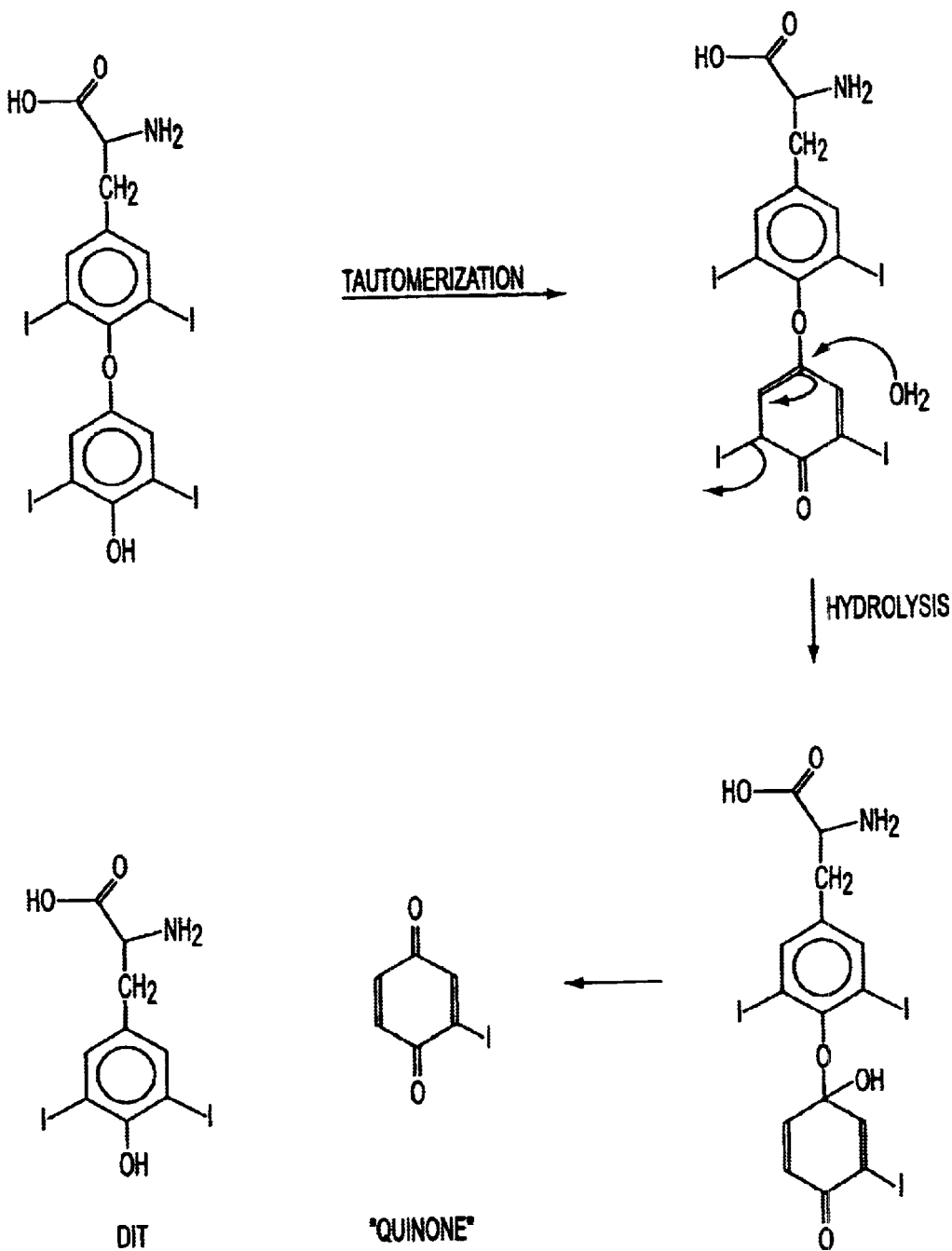
FIG. 1 shows the pathway of the degradation of T4. Following tautomerization of T4, the intermediate is subjected to hydrolysis, to produce DIT and a quinone.
Figure 2:
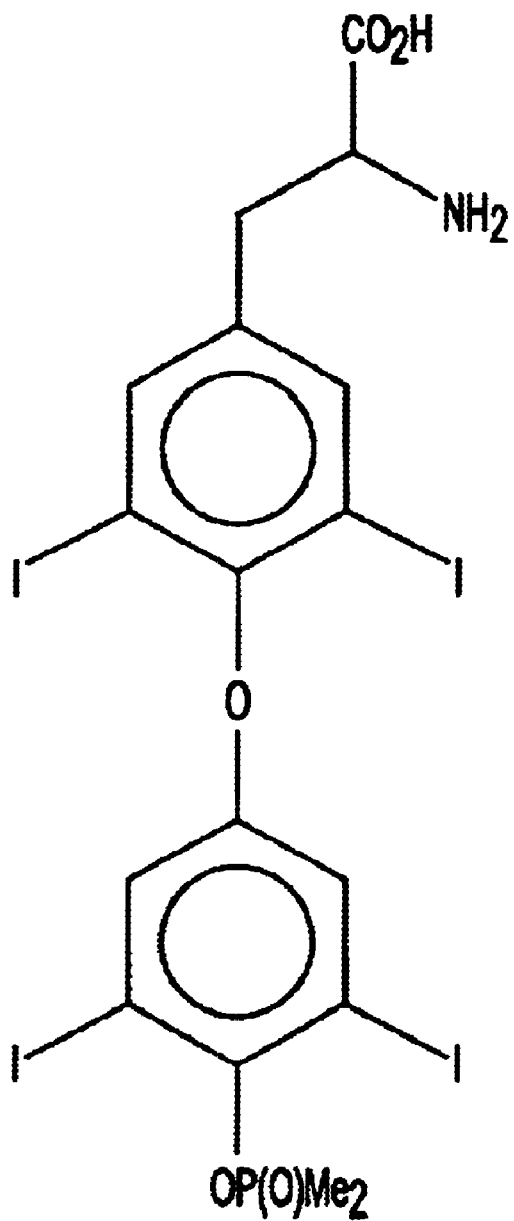
FIG. 2 is the dimethylphosphinate of T4, thyroxinyldimethylphosphinate.
Figure 3:
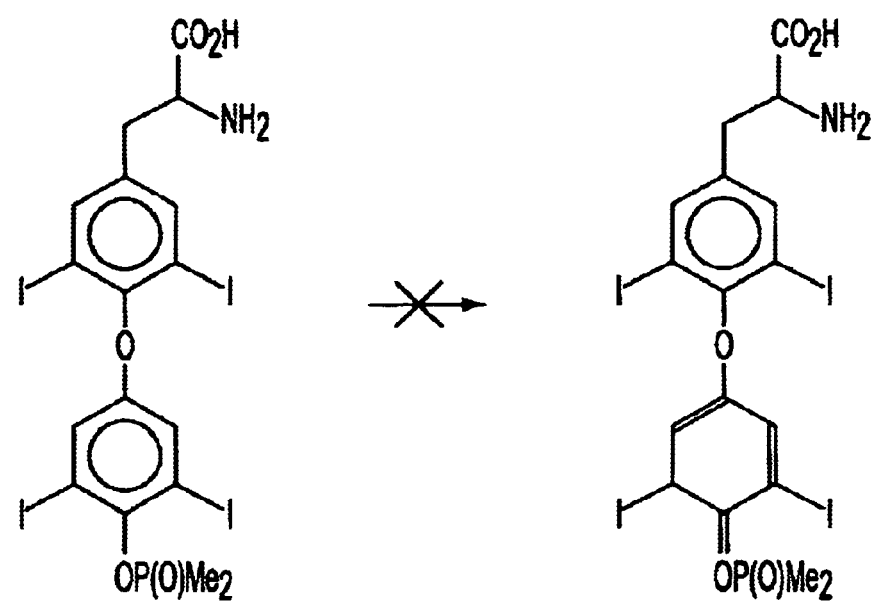
FIG. 3 shows the phosphinate-protected T4 and its inability to tautomerize.

The present invention is practiced by using phosphinate protecting groups to protect against the decomposition of thyroxine and related compounds. These related compounds are preferably other iodothyronines, such as triiodothyronine (T3), 3,5-diiodothyronine (3,5-T2), 3,3'-diiodothyronine (3,3'-T2), reverse triiodothyronine (3,3',5'-triiodothyronine, rT3), and 3-monoiodothyronine (3-T1). The related compounds are also meant to include amino acids such as thyronine, diiodotyrosine, and iodotyrosine, and may include any amino acid that is unstable in the presence of trace amounts of water.

To practice this invention, thyroxine or a related compound is reacted with a dialkyl-or diaryl-phosphinate compound, such as a dialkyl- or diaryl-phosphinic chloride. Most preferably, the dialkyl group is dimethyl or diethyl. The alkyl group may also be any hydrocarbon, preferably C1 to C18, comprising either straight chained, branched chained, or cyclic compounds, optionally substituted with oxygen-, phosphorus-, sulfur- and nitrogen-containing groups. The aryl group may be any aromatic group, preferably phenyl, and may be optionally substituted with alkyl or additional phenyl groups, and may also be optionally substituted with oxygen-, phosphorus-, sulfur- and nitrogen-containing groups. The two alkyl groups may be the same or different. There may also be one alkyl and one aryl group on the phosphinate. The dimethyl can be replaced with diphenyl, diethyl or any other dialkyl and get the same level of protection on T4. In addition, the phosphinate group can be replaced with a similarly substituted dialkyl-, diaryl-, or alkylaryl-phosphate group. Other groups that can be used instead of the phosphinate group include acetyl, trialkylsilyl, and benzyloxy carbonyl.

Although N-protection may not be necessary, the best yield of throxinyldialkylphosphinate is achieved by first protecting the nitrogen of T4 or related compound. Any method of protecting the nitrogen of an amino acid group known in the art may be employed in protecting the nitrogen of thyroxine and related compounds. Most preferably, the reagent of choice is trimethylsilylethoxycarbonyloxysuccinimide. The N-protected T4 is then treated with dimethylphosphinic chloride or diphenylphosphinic chloride, as before, and the product of this reaction is N-deprotected by treatment with trifluoroacetic acid. Deprotection can also take place using other mild acids, as well.

The invention thus provides a method to stabilize and increase the shelf life of thyroxine and related thyroid hormone products. The compositions of the present invention will be used in methods of treating hypothyroidism. These products will be used at levels similar to those used in treating hypothyroid patients with Synthroid. Determining the precise levels to be used in a particular patient may be accomplished using methods well known to those of skill in the art, including monitoring the levels of thyroid hormones in the blood using known techniques and adjusting the dosage accordingly to get blood levels within acceptable limits. The compositions will be particularly useful in providing injectable. and oral suspension formulations, as well as tablets, for thyroid hormones.

The invention will now be illustrated by, but is not intended to be limited to, the following examples.

EXAMPLES

Example 1

Preparation of 2-trimethylsilylethyl Carbonochloridate (Teoc-Cl)

To a solution of 2-trimethylsilylethanol (5.0 g, 42.3 mmol) in dichloromethane (35 mL) at 0° C. was added triethylamine (4.7 g, 46.5 mmol). To this stirred solution was added dropwise a solution of triphosgene (4.40 g, 14.8 mmol) in dichloromethane (15 mL); a white precipitant was formed immediately. The mixture was stirred at low temperature for 15 minutes, the ice bath removed, and the mixture was stirred for an additional 1 hour at room temperature. After 1 hour, the white precipitant was filtered and washed with dichloromethane (~60 mL). The combined filtrate and washings were concentrated. The resultant oily carbonochloridate was used without further purification.

Example 2

Preparation of 1-[2(Trimethylsilyl) ethoxycarbonyloxy]pyrrolidin-2,5-dione (Teoc-0Su)

2-Trimethylsilylethyl carbonochloridate (4.8 g, 26.9 mmol) was taken up in dry acetonitrile (50 mL). The solution was cooled to 0° and solid N-hydroxysuccinimide (4.0 g, 34.8 mmol) was added with vigorous stirring followed by a solution of dry triethylamine (3.2 g, 31.6 mmol) in dry acetonitrile (5 mL). The mixture was stirred at low temperature for 15 minutes, then at room temperature overnight. The mixture was poured into water (200 ml) and extracted with ether (4×50 mL). The organic extracts were combined, washed with water (2×60 mL), 1 normal hydrochloric acid (60 mL), again water (60 mL), brine (60 mL), dried with magnesium sulfate and evaporated to dryness. The residue was taken up in boiling hexane (200 mL) and the solution allowed to cool. Crystallization was completed by storage at −15° C. (yield: 1.70 g).

Example 3

Preparation of N-Trimethylsilylethoxycarbonylthyroxine (Teoc-T4)

To a stirred suspension of thyroxine (1.66 g, 2.14 mmol) in DMSO (15 mL) was added triethylamine (3.21 mmol) followed by solid Teoc-0Su (610 mg, 2.35 mmol). The mixture was stirred at room temperature overnight then diluted with water (22 mL), acidified with saturated potassium hydrogen sulfate solution and extracted with ether (3×45 mL). The combined organic extracts were washed with water (4×45 mL), dried with magnesium sulfate, and evaporated to dryness. (Yield: 1.87 g).

Example 4

Preparation of [N-Trimethylsilylethoxycarbonyl-O-throxinyl]dimethylphosphinate

N-Trimethylsilylethoxycarbonylthyroxine (307 mg, 0.334 mmol) was dissolved in 10 mL dry chloroform, and to the stirred solution was added anhydrous triethylamine (154 μL, 1.10 mmol). After stirring for 10 minutes at room temperature, dimethylphosphinyl chloride (112.7 μL, 1.00 mmol) was added and stirring was continued at room temperature. After 90 minutes, the reaction appeared to be nearly completed by TLC analysis (chloroform/i-propanol/acetic acid, 85:10:5), based on relatively clean conversion of starting material (Rf 0.34) to product (Rf 0.22). The reaction was quenched by the addition of 20 mL 0.5 N HCl. The product was extracted into chloroform (3×30 mL). The combined chloroform layers were washed with brine, dried over magnesium sulfate and evaporated to dryness, affording 280 mg [N-trimethylsilylethoxycarbonyl-O-throxinyl] dimethylphosphinate (84% yield).

Example 5

Preparation of O-Thyroxinyldimethylphosphinate

[N-Trimethylsilylethoxycarbonyl-O-thyroxinyl] dimethylphosphinate (42 mg, 0.042 mmol) was dissolved in 1.5 mL of trifluoroacetic acid. After 5 minutes stirring at room temperature, TLC analysis (chloroform/i-propanol/acetic acid, 85:10:5) showed the deprotection to be complete. The solvent was removed by rotary evaporation. Azeotropic evaporation with hexane afforded the product as a fine, white powder in nearly quantitaive yield. NMR analysis showed the product to be the desired O-thyroxinyldimethylphosphinate.

What is claimed is:

1. A composition comprising thyroxine protected at a phenolic hydroxyl with a protecting group, wherein said protecting group is a dialkylphosphinate.

2. The composition of claim 1, wherein said dialkylphosphinate is dimethylphosphinate.

3. The composition of claim 1, wherein said dialkylphosphinate is diethylphosphinate.

4. A method of stabilizing and increasing the shelf life of a thyroid hormone comprising protecting thyroxine with a protecting group at a phenolic hydroxyl, wherein said protecting group is a dialkylphosphinate.

5. The method of claim 4, wherein said dialkylphosphinate is dimethylphosphinate.

6. The method of claim 4, wherein said dialkylphosphinate is diethylphosphinate.

7. A pharmaceutical composition comprising a thyroxine protected with a protecting group at a phenolic hydroxyl, wherein said protecting group is a dialkylphosphinate; and a pharmaceutically acceptable excipient.

8. The pharmaceutical composition of claim 7, wherein said dialkylphosphinate is dimethylphosphinate.

9. The pharmaceutical composition of claim 7, wherein said dialkylphosphinate is diethylphosphinate.

10. The pharmaceutical composition of claim 7, 8, or 9 wherein said composition is in the form of an ingestible tablet.

11. The pharmaceutical composition of claim 7, 8, or 9 wherein said composition is in the form of an intravenous preparation.

12. The pharmaceutical composition of claim 7, 8, or 9 wherein said composition is in the form of an oral suspension.

13. A method of treating hypothyroidism comprising administering to a patient in need thereof a thyroxine protected at a phenolic hydroxyl, wherein said protecting group is a dialkylphosphinate.

14. The method of claim 13, wherein said dialkylphosphinate is dimethylphosphinate.

15. The method of claim 13, wherein said dialkylphosphinate is diethylphosphinate.

16. The method of claim 13, 14, or 15 wherein said thyroxine is administered in the form of an ingestible tablet.

17. The method of claim 13, 14, or 15 wherein said thyroxine is administered in the form of an intravenous preparation.

18. The method of claim 13, 14, or 15 wherein said thyroxine is administered in the form of an oral suspension.

19. A composition comprising thyroxine protected at a phenolic hydroxyl with a protecting group, wherein said protecting group is a dialkylphosphate.

20. The composition of claim 19, wherein said dialkylphosphate is dimethylphosphate.

21. The composition of claim 19, wherein said dialkylphosphate is diethylphosphate.

22. A method of stabilizing and increasing the shelf life of a thyroid hormone comprising protecting thyroxine with a protecting group at a phenolic hydroxyl, wherein said protecting group is a dialkylphosphate.

23. The method of claim 22, wherein said dialkylphosphate is dimethylphosphate.

24. The method of claim 22, wherein said dialkylphosphate is diethylphosphate.

25. A pharmaceutical composition comprising a thyroxine protected with a protecting group at a phenolic hydroxyl, wherein said protecting group is a dialkylphosphate; and a pharmaceutically acceptable excipient.

26. The pharmaceutical composition of claim 25, wherein said dialkylphosphate is dimethylphosphate.

27. The pharmaceutical composition of claim 25, wherein said dialkylphosphate is diethylphosphate.

28. The pharmaceutical composition of claim 25, 26, or 27 wherein said composition is in the form of an ingestible tablet.

29. The pharmaceutical composition of claim 25, 26, or 27 wherein said composition is in the form of an intravenous preparation.

30. The pharmaceutical composition of claim 25, 26, or 27 wherein said composition is in the form of an oral suspension.

31. A method of treating hypothyroidism comprising administering to a patient in need thereof a thyroxine protected at a phenolic hydroxyl, wherein said protecting group is a dialkylphosphate.

32. The method of claim 31, wherein said dialkylphosphate is dimethylphosphate.

33. The method of claim 31, wherein said dialkylphosphate is diethylphosphate.

34. The method of claim 31, 32, or 33 wherein said thyroxine is administered in the form of an ingestible tablet.

35. The method of claim 31, 32, or 33 wherein said thyroxine is administered in the form of an intravenous preparation.

36. The method of claim 31, 32, or 33 wherein said thyroxine is administered in the form of an oral suspension.

37. A composition comprising iodotyrosine protected at a phenolic hydroxyl with a protecting group, wherein said protecting group is a dialkylphosphinate.

38. The composition of claim 37, wherein said dialkylphosphinate is dimethylphosphinate.

39. The composition of claim 37, wherein said dialkylphosphinate is diethylphosphinate.

40. A method of stabilizing and increasing the shelf life of a thyroid hormone comprising protecting iodotyrosine with a protecting group at a phenolic hydroxyl, wherein said protecting group is a dialkylphosphinate.

41. The method of claim 40, wherein said dialkylphosphinate is dimethylphosphinate.

42. The method of claim 40, wherein said dialkylphosphinate is diethylphosphinate.

43. A pharmaceutical composition comprising a iodotyrosine protected with a protecting group at a phenolic hydroxyl, wherein said protecting group is a dialkylphosphinate; and a pharmaceutically acceptable excipient.

44. The pharmaceutical composition of claim 43, wherein said dialkylphosphinate is dimethylphosphinate.

45. The composition of claim 43, wherein said dialkylphospinate is diethylphosphinate.

46. The pharmaceutical composition of claim 43, 44, or 45 wherein said composition is in the form of an ingestible tablet.

47. The pharmaceutical composition of claim 43, 44 or 45 wherein said composition is in the form of an intravenous preparation.

48. The pharmaceutical composition of claim 43, 44, or 45 wherein said composition is in the form of an oral suspension.

49. A method of treating hypothyroidism comprising administering to a patient in need thereof an iodotyrosine protected at a phenolic hydroxyl, wherein said protecting group is a dialkylphosphinate.

50. The method of claim 49, wherein said dialkyphosphinate is dimethylphosphinate.

51. The method of claim 49, wherein said dialkylphosphinate is diethylphosphinate.

52. The method of claim 49, 50, or 51 wherein said iodotyrosine is administered in the form of an ingestible tablet.

53. The method of claim 49, 50 or 51 wherein said iodotyrosine is administered in the form of an intravenous preparation.

54. The method of claim 49, 50, or 51 wherein said iodotyrosine is administered in the form of an oral suspension.

55. A composition comprising iodotyrosine protected at a phenolic hydroxyl with a protecting group, wherein said protecting group is a dialkylphosphate.

56. The composition of claim 55, wherein said dialkylphosphate is dimethylphosphate.

57. The composition of claim 55, wherein said dialkylphosphate is diethylphosphate.

58. A method of stabilizing and increasing the shelf life of a thyroid hormone comprising protecting iodotyrosine with a protecting group at a phenolic hydroxyl, wherein said protecting group is a dialkylphosphate.

59. The method of claim 58, wherein said dialkylphosphate is dimethylphosphate.

60. The method of claim 58, wherein said dialkylphosphate is diethylphosphate.

61. A pharmaceutical composition comprising an iodotyrosine protected with a protecting group at a phenolic hydroxyl, wherein said protecting group is a dialkylphosphate; and a pharmaceutically acceptable excipient.

62. The pharmaceutical composition of claim 61, wherein said dialkylphosphate is dimethylphosphate.

63. The pharmaceutical composition of claim 61, wherein said dialkylphosphate is diethylphosphate.

64. The pharmaceutical composition of claim 61, 62, or 63 wherein said composition is in the form of an ingestible tablet.

65. The pharmaceutical composition of claim 61, 62, or 63 wherein said composition is in the form of an intravenous preparation.

66. The pharmaceutical composition of claim 61, 62, or 63 wherein said composition is in the form of an oral suspension.

67. A method of treating hypothyroidism comprising administering to a patient in need thereof an iodotyrosine protected at a phenolic hydroxyl, wherein said protecting group is a dialkylphosphate.

68. The method of claim 67, wherein said dialkylphosphate is dimethylphosphate.

69. The method of claim 67, wherein said dialkylphosphate is a diethylphosphate.

70. The method of claim 67, 68, or 69 wherein said iodotyrosine is administered in the form of an ingestible tablet.

71. The method of claim 67, 68, or 69 wherein said iodotyrosine is administered in the form of an intravenous preparation.

72. The method of claim 67, 68, or 69 wherein said iodotyrosine is administered in the form of an oral suspension.

73. A composition comprising diiodotyrosine protected at a phenolic hydroxyl with a protecting group, wherein said protecting group is a dialkylphosphinate.

74. The composition of claim 72, wherein said dialkylphosphinate is dimethylphosphinate.

75. The composition of claim 72, wherein said dialkylphosphinate is diethylphosphinate.

76. A method of stabilizing and increasing the shelf life of a thyroid hormone comprising protecting diiodotyrosine with a protecting group at a phenolic hydroxyl, wherein said protecting group is a dialkylphosphinate.

77. The method of claim 76, wherein said dialkylphosphinate is dimethylphosphinate.

78. The method of claim 76, wherein said dialkylphosphinate is diethylphosphinate.

79. A pharmaceutical composition comprising a diiodotyrosine protected with a protecting group at a phenolic hydroxyl, wherein said protecting group is a dialkylphosphinate; and a pharmaceutically acceptable excipient.

80. The pharmaceutical composition of claim 79, wherein said dialkylphosphinate is dimethylphosphinate.

81. The pharmaceutical composition of claim 79, wherein said dialkylphosphinate is diethylphosphinate.

82. The pharmaceutical composition of claim 79, 80, or 81 wherein said composition is in the form of an ingestible tablet.

83. The pharmaceutical composition of claim 79, 80, or 81 wherein said composition is in the form of an intravenous preparation.

84. The pharmaceutical composition of claim 79, 80 or 81 wherein said composition is in the form of an oral suspension.

85. A method of treating hypothyroidism comprising administering to a patient in need thereof a diiodotyrosine protected at a phenolic hydroxyl, wherein said protecting group is a dialkylphosphinate.

86. The method of claim 85, wherein said dialkylphosphinate is dimethylphosphinate.

87. The method of claim 85, wherein said dialkylphosphinate is diethylphosphinate.

88. The method of claim 85, 86, or 87 wherein said diiodotyrosine is administered in the form of an ingestible tablet.

89. The method of claim 85, 86, or 87 wherein said diiodotyrosine is administered in the form of an intravenous preparation.

90. The method of claim 85, 86, or 87 wherein said diiodotyrosine is administered in the form of an oral suspension.

91. A composition comprising diiodotyrosine protected at a phenolic hydroxyl with a protecting group, wherein said protecting group is a dialkylphosphate.

92. The method of claim 91, wherein said dialkylphosphate is dimethylphosphate.

93. The method of claim 91, wherein said dialkylphosphate is diethylphosphate.

94. A method of stabilizing and increasing the shelf life of a thyroid hormone comprising protecting diiodotyrosine with a protecting group at a phenolic hydroxyl, wherein said protecting group is a dialkylphosphate.

95. The pharmaceutical composition of claim 94, wherein said dialkylphosphate is dimethylphosphate.

96. The pharmaceutical composition of claim 94, wherein said dialkylphosphate is diethylphosphate.

97. A pharmaceutical composition comprising a diiodotyrosine protected with a protecting group at a phenolic hydroxyl, wherein said protecting group is a dialkylphosphate; and a pharmaceutically acceptable excipient.

98. The pharmaceutical composition of claim 97, wherein said dialkylphosphate is dimethylphosphate.

99. The pharmaceutical composition of claim 97, wherein said dialkylphosphate is diethylphosphate.

100. The pharmaceutical composition of claim 97, 98, or 99 wherein said composition is in the form of an ingestible tablet.

101. The pharmaceutical composition of claim 97, 98, or 99 wherein said composition is in the form of an intravenous preparation.

102. The pharmaceutical composition of claim 97, 98, or 99 wherein said composition is in the form of an oral suspension.

103. A method of treating hypothyroidism comprising administering to a patient in need thereof a diiodotyrosine protected at a phenolic hydroxyl, wherein said protecting group is a dialkylphosphate.

104. The method of claim 103, wherein said dialkylphosphate is dimethylphosphate.

105. The method of claim 103, wherein said dialkylphosphate is diethylphosphate.

106. The method of claim 103, 104, or 105 wherein said diiodotyrosine is administered in the form of an ingestible tablet.

107. The method of claim 103, 104, or 105 wherein said diiodotyrosine is administered in the form of an intravenous preparation.

108. The method of claim 103, 104, or 105 wherein said diiodotyrosine is administered in the form of an oral suspension.

* * * * *